(12) United States Patent
Perez et al.

(10) Patent No.: US 9,804,117 B2
(45) Date of Patent: Oct. 31, 2017

(54) $CO_2$ CONCENTRATION MEASUREMENT IN DRY GAS MIXTURES (71) Applicant: SCHLUMBERGER TECHNOLOGY CORPORATION, Sugar Land, TX (US)

(72) Inventors: Albert Perez, Brookfield, CT (US); Terizhandur S. Ramakrishnan, Boxborough, MA (US); Wenlin Zhang, Houston, TX (US); Li Jiang, Katy, TX (US); Roy Koveleski, Danbury, CT (US); Quincy K. Elias, Mattapan, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 622 days.

(21) Appl. No.: 13/966,093

(22) Filed: Aug. 13, 2013

(65) Prior Publication Data

US 2015/0047990 A1    Feb. 19, 2015

(51) Int. Cl.
G01N 27/403    (2006.01)
G01N 27/407    (2006.01)

(52) U.S. Cl.
CPC ....... *G01N 27/403* (2013.01); *G01N 27/4074* (2013.01)

(58) Field of Classification Search
None
See application file for complete search history.

(56) References Cited

U.S. PATENT DOCUMENTS

| 3,598,711 | A | | 8/1971 | Flais |
| 3,616,408 | A | * | 10/1971 | Hickam ................. F23N 5/006 137/93 |
| 3,616,413 | A | | 10/1971 | Reichner |
| 4,377,460 | A | | 3/1983 | Hirayama et al. |
| 4,855,034 | A | | 8/1989 | Sugimoto et al. |

(Continued)

FOREIGN PATENT DOCUMENTS

| EP | 0060944 A1 | 9/1982 |
| EP | 0073153 A2 | 3/1983 |

(Continued)

OTHER PUBLICATIONS

Fujita (JPH02213763), a translation into English is proved with this office action.*

(Continued)

*Primary Examiner* — Luan Van
*Assistant Examiner* — Steven E Rosenwald (57) ABSTRACT

Described herein is an apparatus and methods for characterizing a fluid composition including exposing electrolyte to one fluid mixture, collecting a signal from an electrode in contact with the electrolyte, and simultaneously exposing the electrolyte to a second fluid, collecting a signal from a second electrode in contact with the electrolyte exposed to the second fluid, and comparing the signal difference between the electrodes with the Nerst equation wherein the temperature of the electrolyte is above 488° C. Carbon dioxide, nitrogen, and/or oxygen may be present in the fluid and/or the second fluid.

28 Claims, 9 Drawing Sheets

(56) References Cited

U.S. PATENT DOCUMENTS

| | | | |
|---|---|---|---|
| 4,985,126 A * | 1/1991 | Haefele | G01N 27/4074 204/406 |
| 6,241,873 B1 * | 6/2001 | Namba | G01N 27/4074 204/421 |
| 8,057,653 B2 | 11/2011 | Dutta et al. | |
| 2003/0121780 A1 * | 7/2003 | Dutta | C04B 35/486 204/424 |
| 2003/0206026 A1 | 11/2003 | Diakonov et al. | |
| 2008/0165356 A1 | 7/2008 | Difoggio et al. | |
| 2008/0245666 A1 | 10/2008 | Diehl et al. | |
| 2009/0095626 A1 | 4/2009 | Dutta et al. | |
| 2011/0226042 A1 | 9/2011 | Yu et al. | |
| 2012/0081699 A1 | 4/2012 | Ford et al. | |

FOREIGN PATENT DOCUMENTS

| | | |
|---|---|---|
| JP | 2000275213 | 10/2000 |
| JP | 2004170230 | 6/2004 |

OTHER PUBLICATIONS

Ganthier et al. (J. Electrochem. Soc., 1977, 124/10, pp. 1579-1583).*

International Search Report and Written Opinion for corresponding PCT Application Serial No. PCT/US2014/050059 dated Nov. 19, 2014, 17 pages.

Chen et al., Coupled Experimental Study and Thermodynamic Modeling of Melting Point and Thermal Stability of Li2CO3-Na2CO3-K2CO3 Based Salts, J. Sol. Energy Eng 136(3), Mar. 10, 2017 (May 2, 2014) 7 pages.

Bard et al, Electrochemical Methods Fundamentals and Applications, Wiley & Sons, Inc., (1980) pp. 51-53.

Selman et al, "Physical Chemistry and Electrochemistry of Alkali Carbonate Melts", Advances in Molten Salt Chemistry, edited by G. Mamantov, J., Braunstein, C., B. Mamantov, vol. 4, 198, pp. 189-191.

* cited by examiner

CO₂ CONCENTRATION MEASUREMENT IN DRY GAS MIXTURES

FIELD

Embodiments herein relate to methods for monitoring carbon dioxide concentration in fluid streams using an electrochemical method. It is readily adapted for laboratory, wellbore, carbon dioxide pipeline, and flue-gas applications.

BACKGROUND

Measurement of $CO_2$ concentration in pipeline streams is useful and necessary for a variety of reasons. The heating value of the natural gas stream, or more appropriately the standard heat of combustion, deteriorates with increasing $CO_2$ concentration.

In many $CO_2$ injection projects, methane is present in a recycle stream. Composition of the gas stream is regularly monitored for both separator operation and termination of inefficient recycling of $CO_2$. Furthermore, in some applications, the phase behavior of the gas stream is altered sufficiently to have a material effect on operational design.

In contrast, many gas wells produce $CO_2$ with methane and other gaseous light hydrocarbons. In these applications, a downhole measurement of periodic gas samples or an in-line continuous measurement is valuable. Likewise, in monitoring applications for fields undergoing $CO_2$ injection, a robust method capable of quantitative determination for evaluating migration of $CO_2$ is essential. In these applications, sensor sensitivity spanning the entire range of mole fractions is required.

The Japanese patent application publication number 2000275213A uses a dual molten carbonate cell where a first carbonate is dissociated to generate $CO_2$ and $O_2$ by applying a small current of about 10 mA. Another cell is used to measure the junction potential across the second cell's electrolyte in contact with the reference gas stream and the sampled gas. The interpretation of the measured potential relies on small levels of $CO_2$ concentration, typical of what is found in the atmosphere. The mechanical assembly is not designed to withstand a pressure differential between the reference and sampling compartments.

The Japanese patent application publication number 2004170230A proposes a $CO_2$ sensor using electrodes with a film coated with a thick conductive ceramic, NASICON™ This type of apparatus generally suffers from limited performance in the presence of water vapor due to the deterioration of NASICON™ with moisture.

United States Patent Application Publication Number 20090095626A1 uses a sensor structure containing lithium phosphate as electrolyte and a mixture of lithium and barium carbonates as electrode surface coating materials. The reference electrode is a lithium titanate-titanium dioxide mixture. It operates at 500° C. This application's focus is structuring a carbonate electrode layer that had reduced sensitivity to humidity.

These references are applicable when the systems are at a low pressure, and the systems are designed to operate for dilute $CO_2$ concentration in the gas stream. Furthermore, the sensors are slow to respond, often requiring minutes. Given the corrosive nature of the electrolyte, feeding two different gas streams and preventing electrolyte migration beyond its housing remains an issue.

SUMMARY

Embodiments of the invention relate to an apparatus and methods for characterizing a fluid composition including exposing electrolyte to one fluid with a composition, collecting a signal from an electrode in contact with the electrolyte, exposing the electrolyte to a second fluid, collecting a signal from a second electrode in contact with the electrolyte exposed to the second fluid, and comparing the difference in signals to one using the Nerst equation wherein the temperature of the electrolyte is above 488° C. Carbon dioxide is present in the fluid and/or the second fluid. Embodiments of the invention relate to methods and an apparatus for observing a gas composition including a housing comprising alumina configured to contain electrolyte, inlet and outlet ports in the housing for a fluid with a known composition, second inlet and second outlet ports in the housing for a second fluid wherein the housing directs fluid flow between the inlet and outlet ports and the second fluid flow between the second inlet and second outlet ports, an electrode in contact with the electrolyte in contact with the fluid, and an electrode in contact with the electrolyte in contact with the second fluid.

DETAILED DESCRIPTION

Rapidity, robustness, and balanced high pressure systems are prerequisites in downhole applications for measuring carbon dioxide concentration. Herein, we have shown a sensor assembly that enables us to measure $CO_2$ concentrations is a mixed-gas stream. The sensor electrolyte is an eutectic mixture of carbonate compounds. The assembly is constructed out of nearly inert alumina and provides separate pathways for the sample and reference gases. Incorporating a diffusion controlling communication channel between the two electrolyte compartments provides electrode positioning flexibility. We provide a discussion of the separation and communication geometry of the housing. Additionally, pressure balanced sampling and delivery are also discussed.

Herein, the sensor measures Nernst electrochemical potential using a binary mixture of $Li_2CO_3$ and $K_2CO_3$ as the electrolyte. This carbonate mixture forms an eutectic with a lowest melting point of 488° C. (see e.g. J. R. Selman and H. Maru's article in Advances in Molten Salt Chemistry, edited by G. Mamantov, J., Braunstein, C., B. Mamantov, 4, 1981). Several electrolyte mixture phase diagrams are presented in the reference, but the relevant one is for the $Li_2CO_3$—$K_2CO_3$ mixture). An electrochemical potential develops across the molten electrolyte interfaces when sandwiched by gas streams of two different CO$_2$ concentrations. The magnitude of the potential is given by the Nernst equation. This equation arises by relating the change in the Gibbs free energy (G) from reactants to products to the electrical potential (V) difference between the electrode on the product side to the reactants side of the reaction, i.e., $$\Delta G = -nF\Delta V, \quad (1)$$

where F is the Faraday constant, and n is the stoichiometric coefficient of electrons in the reaction. At standard conditions of reactants and products a subscript 0 is used for G and V, thus defining standard potential with respect to which an electrical potential may be computed for arbitrary concentrations. If the reactant species are labeled $R_i$ and the products $P_j$, with their stoichiometric coefficients being $\alpha_i$ and $\beta_j$, the electrical potential is (See, A. J. Bard and L. R. Faulkner, Electrochemical Methods and Applications, Wiley, 1980), $$V = V_0 - \frac{RT}{nF}\ln\left(\frac{\prod_j a_{P_j}^{\beta_j}}{\prod_i a_{R_i}^{\alpha_i}}\right), \quad (2)$$

where the activity is labeled a. For ideal mixtures, we may replace the activity with partial pressures.

Carbonate mixtures function as electrolyte at unusually high temperatures. For the one considered here, the operational temperature is close to 500° C. Given the corrosive nature of the electrolyte, junction potential measurement is not trivial. Furthermore, mixing between the two gas streams, one of which is the reference, will corrupt the electrical potential measurement. While the concept of the Nernst equation and the junction potential is known, a robust sensor to measure this potential unambiguously is desirable.

We describe a compact sensor that allows us to measure junction potentials rapidly, with equilibration time amounting to seconds. The sensor includes a reference gas stream whose composition is known. In some embodiments, this reference gas is controlled and contacts the first surface of the electrolyte. A gas mixture whose composition is to be determined, henceforth called sampled gas or second fluid, contacts a second surface of the same electrolyte. A Gibbs free energy (G) relationship between the equilibrated concentrations translates to an electrical potential because the interfaces attain chemical equilibrium quickly with the contacting gases. It is this potential that relates the ratios of CO$_2$ concentrations between the gas streams contacting the surfaces. Sampled gas concentration is obtained because the reference gas CO$_2$ fraction is known.

The reference composition may be generated in a number of ways: (i) metered gas from sample chambers carrying pure gases, (ii) premixed gas of known composition, and (iii) chemically or electrochemically generated gas stream where stoichiometric ratios fix the composition. On-demand supply of gas streams is useful in remote locations. Alternatively, in some applications, the reference gas in contact with the first surface may be encapsulated within the sensor, prior to downhole deployment. In some embodiments, we provide the equipment to generate a reference gas containing CO$_2$ and O$_2$ in a particular ratio.

In any event, let us assume an ideal gas mixture. When a molten carbonate mixture is in equilibrium with a stream of gas, in the absence of hydrogen, hydrogen containing compounds, and carbon monoxide, the primary reaction is that of $$CO_2 + \frac{1}{2}O_2 + 2e^- \rightarrow CO_3^{2-}. \quad (3)$$

Consider a molten carbonate electrolyte whose carbonate ions CO$_3^{2-}$ is in equilibrated contact with two different CO$_2$ streams. Herein, the streams are the sample and the reference. The Nernst equation presented above allows us to write the potential between the sample (s) and a reference (r) sides of the electrolyte, equal to $V_s - V_r$. Since $V_0$ is the same for both, assuming ideal mixture, the developed potential becomes $$V_s - V_r = \frac{RT}{2F}\ln\left[\frac{(P^{3/2} yCO_2 y_{O_2}^{1/2})_s}{(P^{3/2} yCO_2 y_{O_2}^{1/2})_r}\right] \quad (4)$$

If the pressure is balanced on both the sample and the reference side, almost a prerequisite if one is required to keep the electrolyte in place, the above equation reduces to $$V_s - V_r = \frac{RT}{2F}\ln\left[\frac{(yCO_2 y_{O_2}^{1/2})_s}{(yCO_2 y_{O_2}^{1/2})_r}\right] \quad (5)$$

We have conducted our experiments with a continuously metered flow q, at standard conditions, of three gases: O$_2$, N$_2$, and CO$_2$. Let $q_t$ denote the total of the rates of the three gases i.e. $q_t = q_{O_2} + q_{CO_2} + q_{N_2}$. Then for an ideal mixture, $$y_i = q_i/q_t \quad (6)$$

where i represents O$_2$ or CO$_2$.

Figure 1:
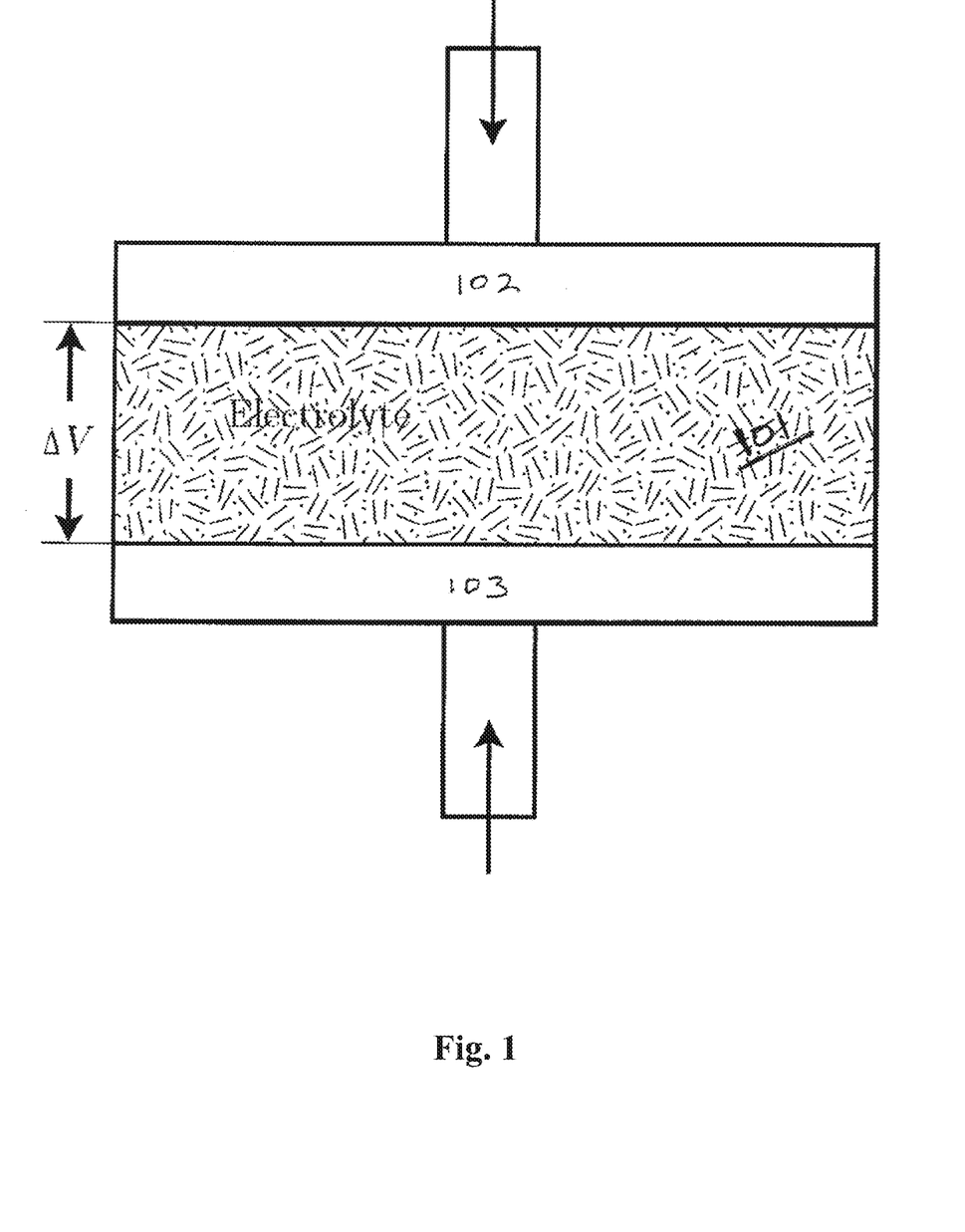
FIG. 1 (Prior Art) is a schematic view of an electrolyte based system to measure the electrochemical potential.

In the schematic configuration of FIG. 1, CO$_2$ on both sides of the electrolyte 101 reacts with the carbonate mixture in the molten state to form carbonate anion. The molten carbonate conducts carbonate anions, whose concentration in equilibrium with the respective gases, sample gas 102 and reference gas 103 sets in an imbalance of electrical potential, in order for the electrochemical potential to be equal. It is important that the configuration is structured so the true junction potential is measured. Ideally, electrodes at the surface of the electrolyte would enable this. But with molten carbonates this is not usually possible, given its unknown wettability, expansion, and gas pressure differences.

While the equilibrium measurements are applicable to a surface potential, in reality, especially in a downhole configuration, and at the operational temperature (500° C.), it is difficult to achieve precise contact with the surface. There is no guarantee of the electrolyte maintaining contact or the electrolyte creeping around the electrode. In the former, the potential obtained is irrelevant and in the latter the magnitude is reduced. Additionally, as the electrolyte melts, a pressure imbalance between the sample and the reference may lead to gas bubbling through the electrolyte resulting in unwanted mixing, sample contamination and therefore reducing the signal magnitude.

We have conducted a number of experiments in a variety of mechanical configurations. Most of these were unreliable. Some of them were unable to prevent mixing of gases through a molten electrolyte and others had difficulty measuring interface potential difference. Based on our laboratory experience, we identified embodiments that provided a high degree of reproducibility with a close match to the theoretically expected values.

Figure 2:
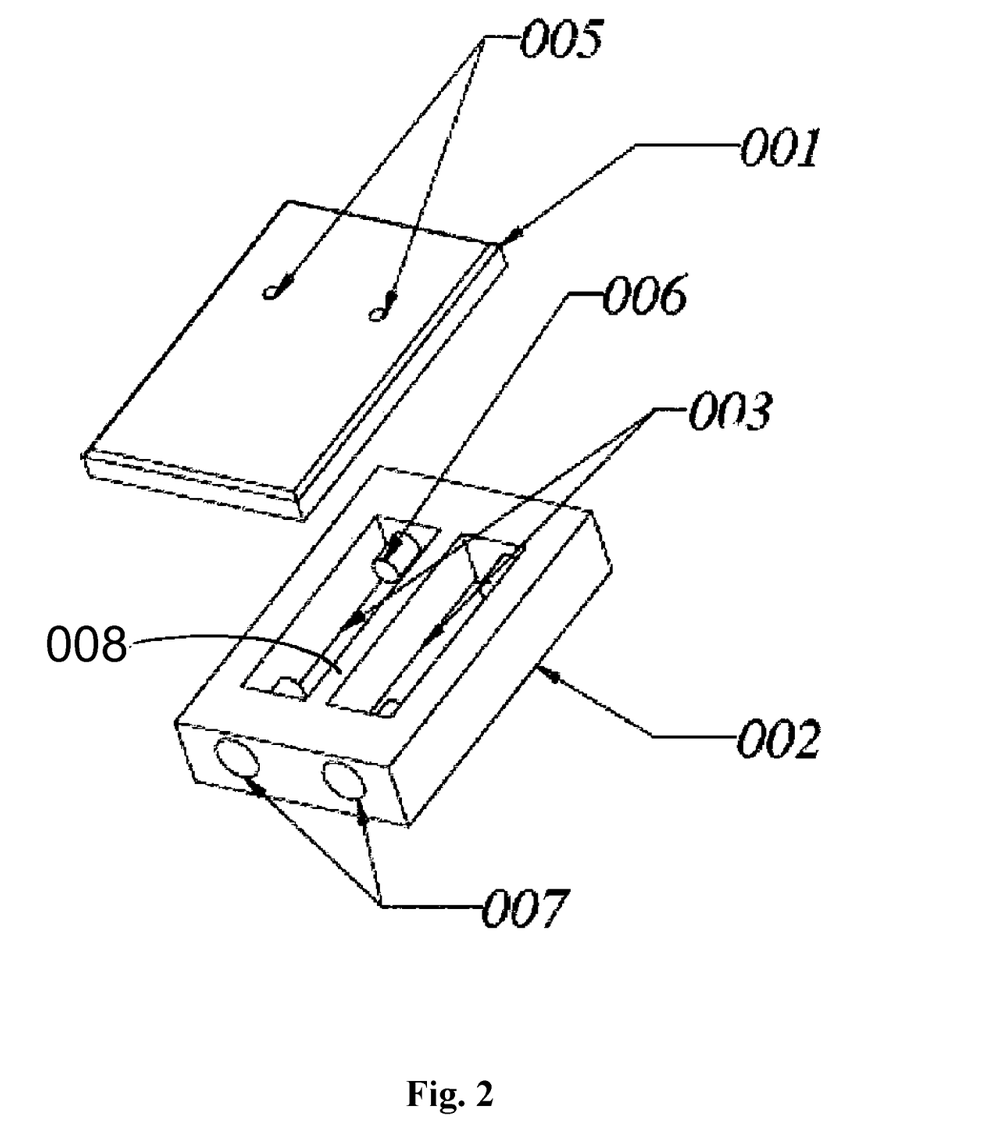
FIG. 2 is an electrolyte based system including a narrow slit for electrolytic communication is provided at the bottom of the partition between the two compartments.

FIG. 2 is a drawing of the sensor device. The body 002 and the tubing (not shown) that provide gas inlet and outlet from the body are made of alumina. Geometrically, the sensor consists of a lid or a cover 001 and the main body 002. The main body 002 has two sections 003, separated by an alumina wall 008 which has a small opening at the bottom for electrolytic continuity (not shown). Our experiments have been conducted with a slit opening at the bottom of the wall; but one may also have a wall with a small orifice opening at the bottom of the wall. The lid 001 has small ports 005 for the electrode wires (not shown), made of gold. There are independent ports 007 for the sample and the reference. The wires make contact with the electrolyte and are slightly immersed in the electrolyte. The electrolyte chambers have a small gas headspace. The gases on either side of the wall do not communicate directly, because the wall is bonded to the lid with a high temperature cement such as Aremco Seal 613. The seal may be undone by raising the temperature past 850° C. and so the sensor may be used, taken apart, cleaned, and refilled. Porous alumina plugs 006 with an average pore size of about 50 µm are provided at the gas inlet and outlet. While the electrochemical potentials are equal for carbonate ions, maximum gradient in chemical potential, or equivalently the electrical potential, is present at the channel, slit, hole or other orifice (not shown). Therefore, the potential difference measured will be nearly equal to what is theoretically expected as the junction potential difference.

Some embodiments may benefit imbedding the molten salt within a porous matrix, such as porous ceramic. By doing so, the movement of the electrolyte is reduced, but still maintains the connections of the electrolyte channel. The electrolyte may be embedded in porous alumina or lithium aluminate in some embodiments.

The device was heated in a furnace (not shown) with temperature control. The furnace is commercially available from Barnstead Thermolyne of Hamsted, N.H. Further, the introduction of the gases to the device was controlled by flow meters including Porter Massflow controller model number MPC95, commercially available from Parker Hannifin of Hatfield, Pa.

The volume of the electrolyte, the housing for the electrolyte, and the overall system are driven by practical constraints. The surface areas of the molten electrolyte in contact with the fluids are much larger than the cross-sectional area afforded by the slit. The gas flow rates are controlled to prevent entrainment of the molten carbonate and fouling of the exit tubing from the system. The volume of the housing of the electrolyte is selected for optimum heat transfer and for heat control. A smaller volume should be selected for tailoring the heat transfer, but, also, the surface area of the carbonate in contact with the gas flows must be large enough for robust contact. A lab bench scale device will have a different volume than devices for wellbore, carbon dioxide pipeline, and flue gas applications.

Variations for the housing design include the following: (i) make the wall thick and have a slit open at the bottom; (ii) rather than a slit have an orifice; keep the orifice sufficiently large that there is no blockage caused by solid electrolyte, but not so large that the orifice is no longer diffusion controlling; (iii) make the wall wedge shaped with the thickest at the bottom so that we may provide sufficient electrolyte, while the orifice at the bottom will be longer in order to be diffusion controlling; and (iv) include gold paste, gold paint, or a combination to replace all or part of the electrodes.

Figure 3:
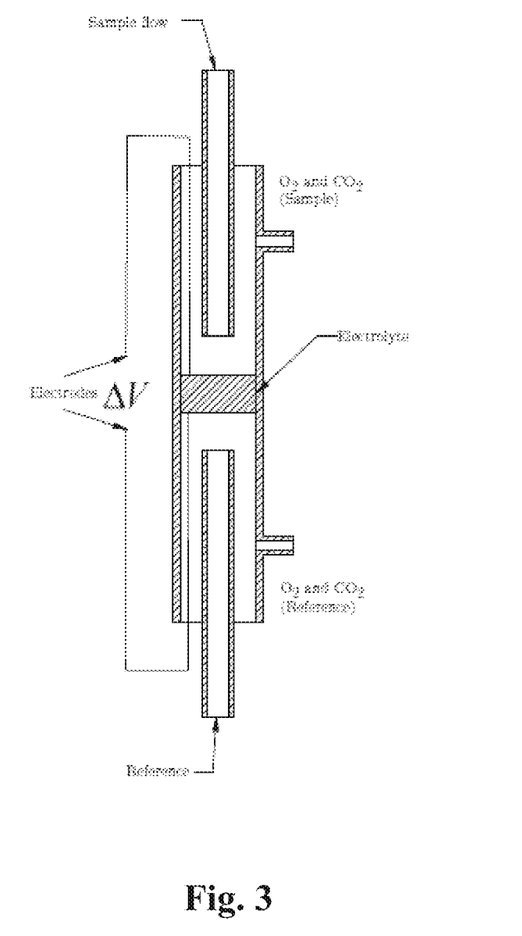
FIG. 3 is a schematic of a tubular arrangement of the electrolyte with gold electrodes.
Figure 4:
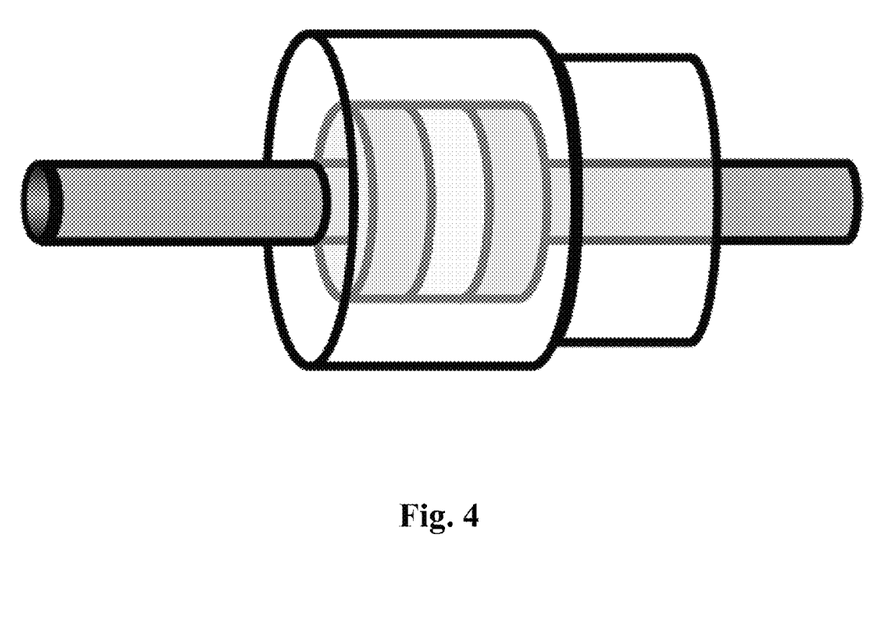
FIG. 4 is a schematic of a tubular gold sandwich arrangement of the electrolyte. For clarity, the outside confining alumina is deliberately shown to be translucent.
Figure 5:
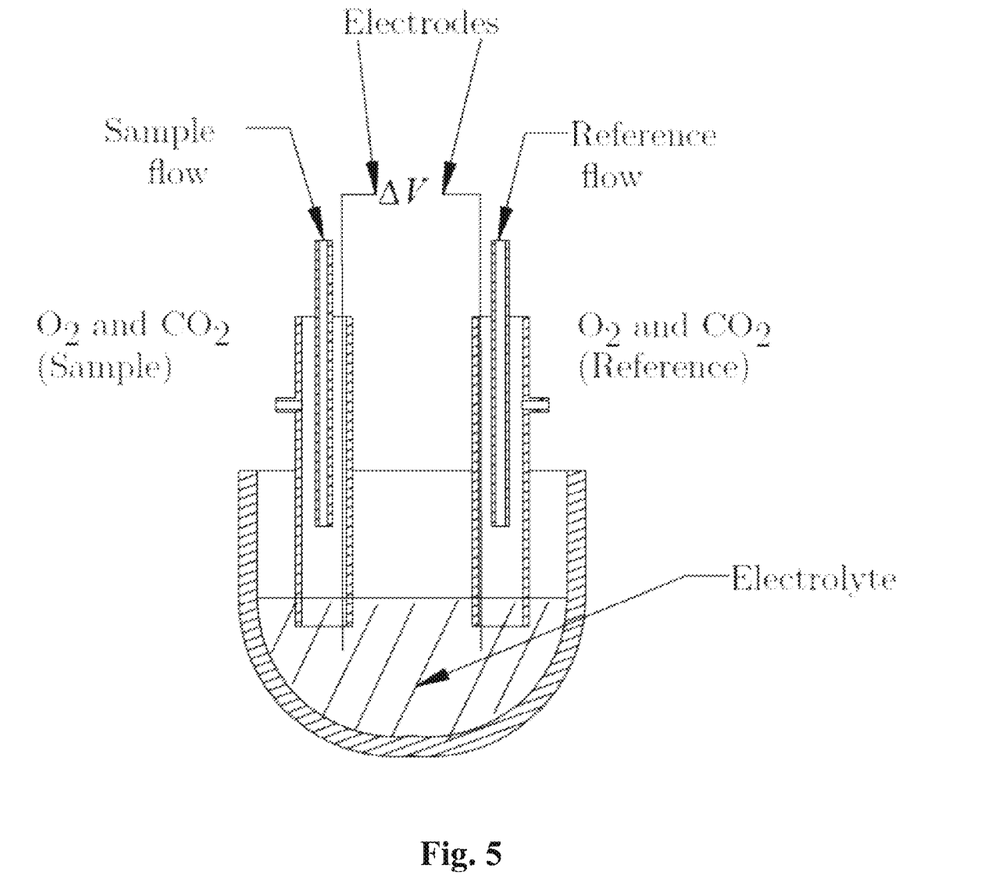
FIG. 5 is a schematic of a sensor in a cell cup.

Other embodiments are shown in FIGS. 3, 4, and 5. FIG. 3 provides a more complicated sensor with an arrangement to have gold discs with tubular gas feed, the discs enveloping the electrolyte and pressed together by male/female alumina cylinders, a picture of which is shown in FIG. 4. With this configuration, each experimental run responded similarly while varying the sample composition, but the numerical value of the data was not in agreement with the theoretical predictions. The configuration of FIG. 5 showed a similar issue, and without a diffusion resistant partition in the electrolyte that is needed between the electrodes, one does not expect the correct electrical potential. Pressure balancing is also required.

Experimental Results

Figure 6:
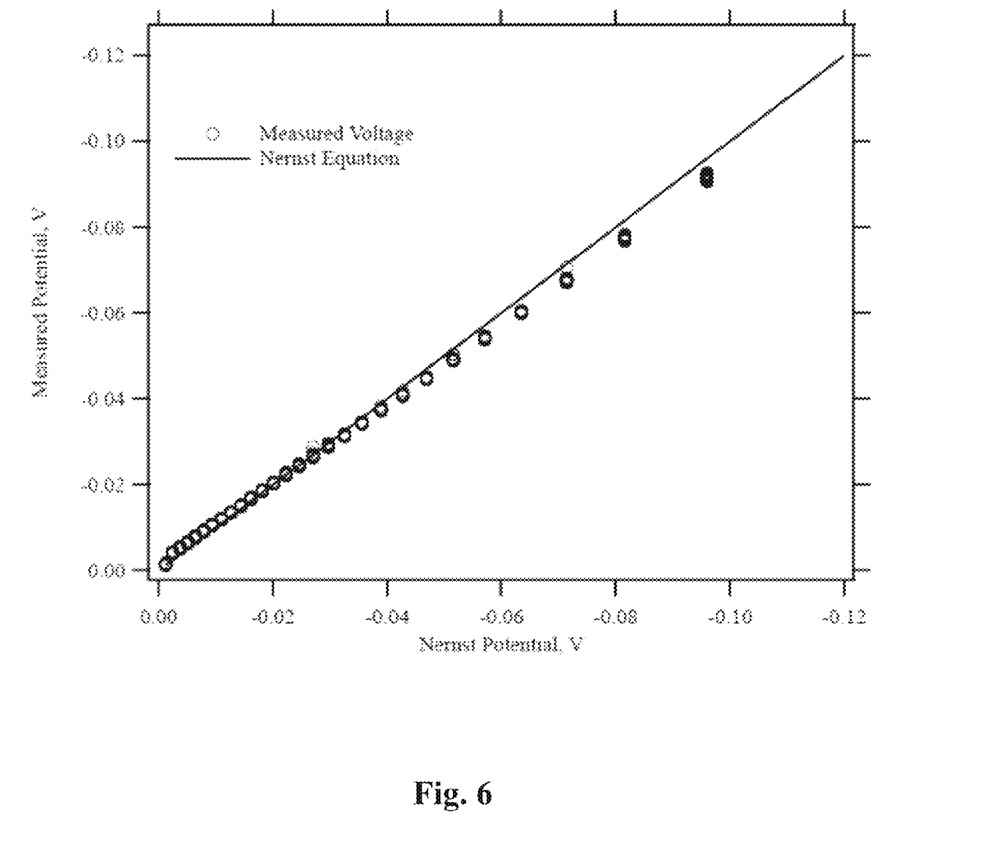
FIG. 6 is a plot of a comparison of Nernst potential with the experimental data.

In all of the experiments, we flowed a mixture of $O_2$, $N_2$ and $CO_2$. No other gases were considered. In all of these cases, knowing the flowing compositions, a theoretical potential may be calculated from the above mentioned Nernst equation 5, and compared to the value of the stabilized measurement. In FIG. 6 we show a comparison with the experimentally obtained points from three different runs with a $CO_2$ mole fraction of 0.022 to 0.667. All of the data following a change in composition on the sample side are shown, including the transient response data, after a change in $CO_2$ mole fraction in the sample stream, except that approximately the first ten seconds of data have been excluded. In about 6 s, the equilibrium potential is established.

Figure 7:
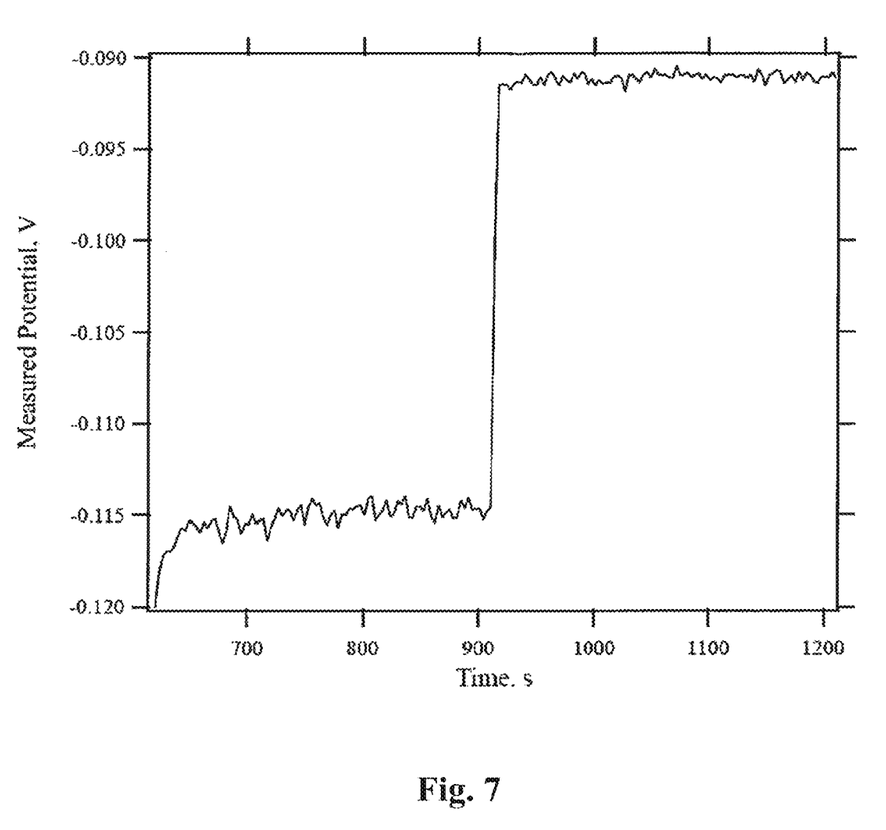
FIG. 7 is a plot of a response for $CO_2$ sample concentration.

To emphasize time evolution, one of the responses is shown in FIG. 7. Rapid approach to equilibrium is evident when sequential changes in composition are made. Stabilization is established in a few seconds. The response is rapid, and by about 6 seconds the voltage obtained is within the noise of the system. The noise is caused by a number of factors: temperature fluctuations, flow rate variations, and noise in the voltage pickup. There is a step change in the $CO_2$ fraction of 2.22 percent to 44 percent at about 910 seconds. It takes about 6 seconds to reach the new equilibrium potential.

Figure 8:
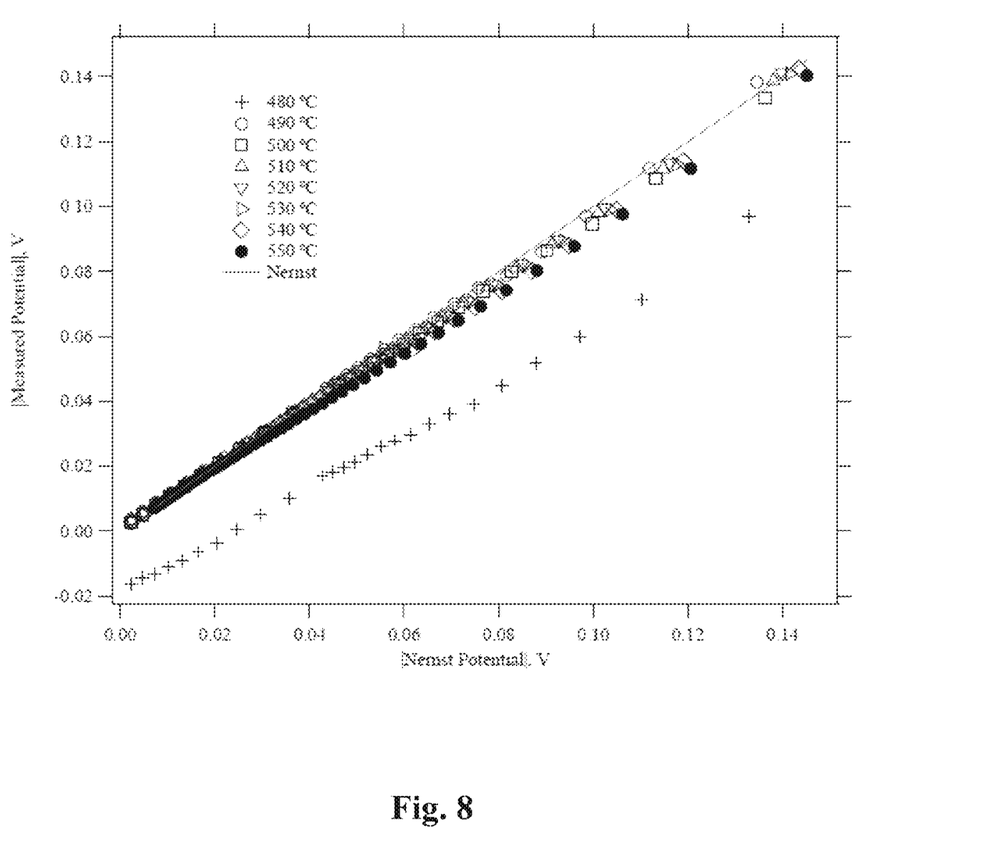
FIG. 8 is a plot of a response for a range of temperatures.

In FIG. 8, we show the comparison between the theoretical and the experimentally obtained values over a range of temperatures. Below 488° C., the electrolyte is a solid, and no interpretable signal is obtained. Here it is quite different from the Nernst potential. The trend is however similar to the equilibrium potential probably because of a low-level electrolytic conduction close to the melting point or variability in temperature. Since the eutectic mixture has a melting point of 488° C., no comparison with Nernst potential is possible. Clearly the data at 480° C. has a large deviation from the calculated Nernst potential. From 490° C. and above the measured values are predicted by the ideal mixture assumption for calculating the equilibrium potential difference.

Thus far, we have tacitly assumed that the sampled gas pressure is the same as that of the reference, necessary for the proper functioning of the carbonate sensor. Otherwise the electrolyte will be displaced to the side with the lower gas pressure, ultimately forcing its way past the porous plugs, and causing undesirable mixing of gas streams. Ultimately, the migration of the electrolyte from the sensor chamber would lead to catastrophic failure, once the electrode contact is lost or if the flow lines are plugged by the solidified electrolyte.

In some embodiments, $P_s$ and $P_r$ are roughly equal; this prevents backflow of the molten carbonate to the gas line. A reservoir supply of reference gas is kept to replenish the reference gas in the chamber when necessary. Through a remotely operable valve, this supply chamber is kept isolated, except for occasional replenishment needs. One embodiment will have a reference chamber with a mixture of gases in the stoichiometric ratio for dissociation of carbonate i.e., a molar ratio of $CO_2$:$O_2$ of 2:1. Then, throughout the monitoring cycle, the reference composition is unlikely to change due to dissociation of the carbonate.

The sample side is also initially filled with the same reference gas at the same pressure $P_r$. In one embodiment, the freshly sampled gas is allowed to accumulate in a separate chamber. By opening an isolation valve, the sampled gas is allowed to replace the previously present gas, at a sufficiently slow rate. We may carry this out with a back pressure from a chamber kept at the same pressure as that of the reference side through digital control of a piston. This prevents appreciable flow of gas towards or away from the reference side and avoids pressure imbalance. Molten carbonate displacement will then be inconsequential.

Figure 9:
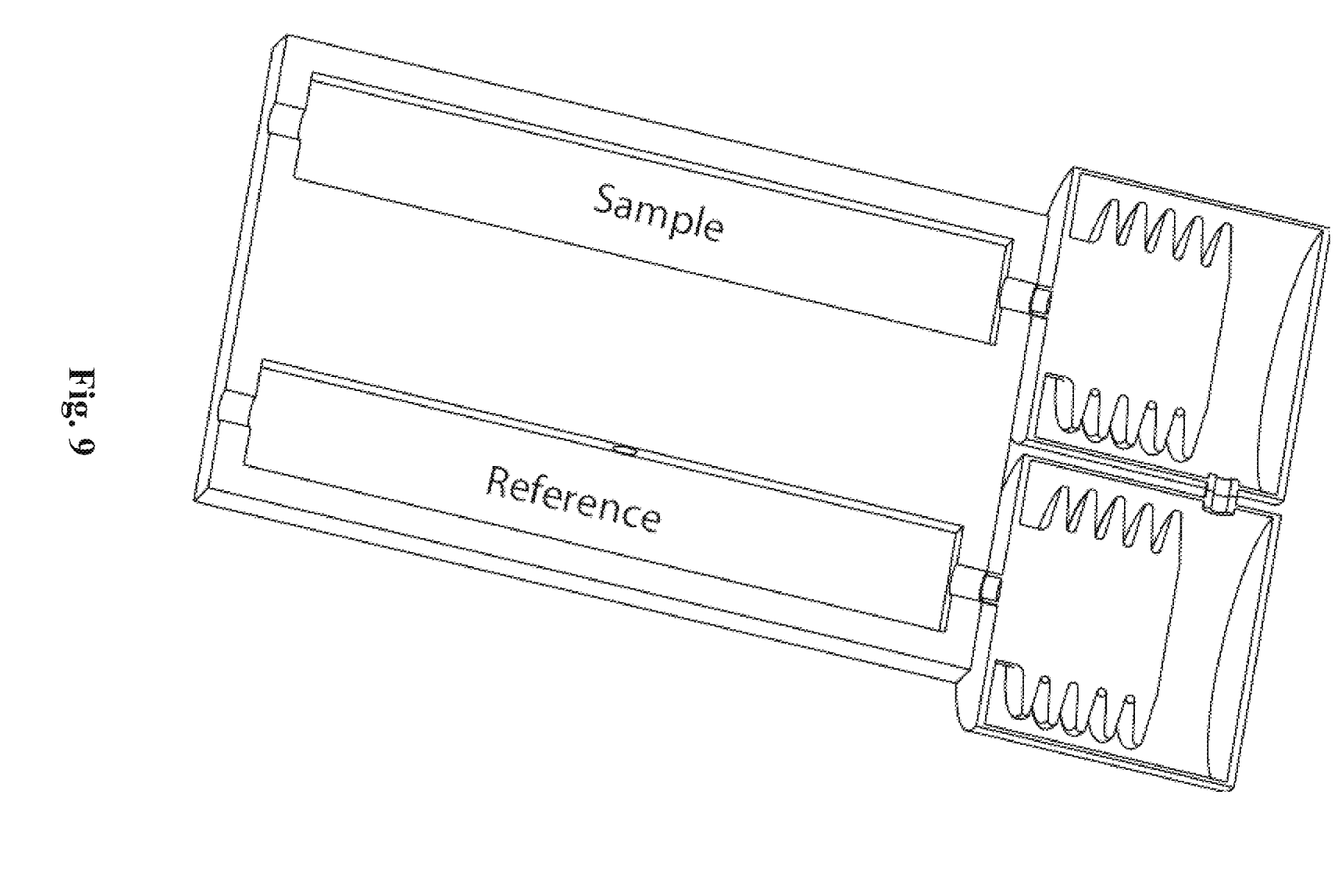
FIG. 9 is a schematic of a pressure balanced sampling system.

Most practical applications will require sequential operation with multiple samples. Prior to deployment within a tool, we suggest bleeding the reference gas from the supply unit to the sensor reference side and the sample side with a common back pressure. This may be carried out at the well-head. Subsequently, we elevate the temperature to just above the melting point of the carbonate. Because of the common back pressure, the pressure in the two systems remain the same. During sample composition determination, the reference line (if necessary; this line need not be replenished) and the sample line are allowed to flow out at a slow flow-rate past the sensor into back-pressure chambers kept at the same pressure. The same back pressure could be enabled by having bellows connecting the two pressure chambers or as mentioned before, or through digitally controlled pistons. An example of the former is provided in FIG. 9. In FIG. 9, gases flow into bellows for which there is a common back-pressure (not shown).

Since the sensors are built for a balanced pressure between sensor internals and the external, it will be preferable to have the entire system under pressure balance, i.e., the gas pressures to be the same as the pressure outside the cell. The outside chamber could be filled with an inert gas, e.g., argon, and may also be pressure balanced with the same back-pressure chamber or a chamber in pressure equilibrium with the back-pressure chamber. Back-pressure magnitude is arbitrary. Some embodiments may benefit when the pressure of the fluid and the second fluid are within 0.5 psi of each other.

Some embodiments may use a controller to provide the comparison between the signals from the electrolyte. The term "controller" should not be construed to limit the embodiments disclosed herein to any particular device type or system. The controller may include a computer system. The computer system may also include a computer processor (e.g., a microprocessor, microcontroller, digital signal processor, or general purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. This memory may be used to store data from transmitted signals, relative signals, and output signals.

Some of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the controller may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

We claim:

1. An apparatus for observing a gas composition, the apparatus comprising:
    a housing comprising alumina configured to contain molten electrolyte, wherein (i) the housing is configured to direct a first fluid through a first flow pathway such that the first fluid contacts the molten electrolyte and (ii) the housing is configured to direct a second fluid through a second flow pathway such that the second fluid contacts the molten electrolyte;
    a first electrode in contact with the molten electrolyte; and
    a second electrode in contact with the molten electrolyte; and
    a pressure balanced sampling system configured to pressure balance the first flow pathway and the second flow pathway.

2. The apparatus of claim 1, wherein the housing comprises a wall to divide the first flow pathway and the second flow pathway.

3. The apparatus of claim 1, further comprising a non-transitory computing device to measure an electrical signal output from the first electrode and the second electrode.

4. The apparatus of claim 1, wherein the housing comprises a first port for the first fluid and a second port for the second fluid, wherein the first port is connected to a first source of the first fluid and the second port is connected to a second source of the second fluid.

5. The apparatus of claim 4, wherein a first flowmeter controls flow of the first fluid to the first port inlet.

6. The apparatus of claim 4, wherein a second flowmeter controls flow of the second fluid to the second port.

7. The apparatus of claim 1, further comprising a heater.

8. The apparatus of claim 7, wherein the heater heats the housing to a temperature above 480° C.

9. The apparatus of claim 1, wherein the molten electrolyte is selected from the group consisting of lithium carbonate, potassium carbonate, and a combination thereof.

10. The apparatus of claim 1, wherein a portion of the housing containing the molten electrolyte permits molar flux across the molten electrolyte and the portion of the housing.

11. The apparatus of claim 1, wherein a housing volume is suitably dimensioned for use with at least one of a lab bench, wellbore, carbon dioxide pipeline, and flue gas.

12. The apparatus of claim 1, wherein the first fluid comprises a sample gas with carbon dioxide of unknown concentration, and the second fluid comprises a reference gas with carbon dioxide of known concentration.

13. The apparatus of claim 12, further comprising:
a nontransitory computing device configured to determine a concentration of carbon dioxide in the sample gas based on an electrical potential signal output from the first electrode and the second electrode.

14. The apparatus of claim 1, wherein the pressure balanced sampling system comprises a piston configured to pressure balance the first flow pathway and the second flow pathway.

15. The apparatus of claim 1, wherein the pressure balanced sampling system comprises a bellows configured to pressure balance the first flow pathway and the second flow pathway.

16. The apparatus of claim 1, wherein the pressure of the first fluid and the pressure of the second fluid are within 0.5 psi of each other.

17. The apparatus of claim 1, wherein the housing defines a first section and a second section and the molten electrolyte is disposed within the first section and the second section.

18. The apparatus of claim 17, wherein the first flow path flows along the first section such that the first fluid contacts the molten electrolyte in the first section and the the second flow path flows along the second section such that the second fluid contacts the molten elctrolyte in the second section.

19. The apparatus of claim 18, further comprising:
a wall that separates the first flow pathway and the first section from the second flow pathway and the second section.

20. The apparatus of claim 19, wherein the wall comprises a trapezoidal cross-section.

21. The apparatus of claim 19, wherein the wall is configured to maintain electrolyte continuity between the first section and the second section.

22. An apparatus for observing a gas composition, the apparatus comprising:

a housing configured to contain molten electrolyte having a first surface and a second surface;
a first port in the housing for directing a first fluid such that the first fluid contacts the first surface of the molten electrolyte;
a second port in the housing for directing a second fluid such that the second fluid contacts the second surface of the molten electrolyte;
a first electrode in the housing in contact with the first surface of the molten electrolyte; and
a second electrode in the housing in contact with the second surface of the molten electrolyte; and
means for pressure balancing the first fluid and the second fluid.

23. The apparatus of claim 22, wherein the pressure of the first fluid and the pressure of the second fluid are within 0.5 psi of each other.

24. The apparatus of claim 22, wherein the housing defines a first section and a second section and the molten electrolyte is disposed within the first section and the second section.

25. The apparatus of claim 24, wherein the first fluid contacts the first surface of molten electrolyte in the first section and the second fluid contacts the second surface of the molten elctrolyte in the second section.

26. The apparatus of claim 22, wherein the housing comprises alumina.

27. The apparatus of claim 22, wherein the first fluid comprises a sample gas with carbon dioxide of unknown concentration, and the second fluid comprises a reference gas with carbon dioxide of known concentration.

28. The apparatus of claim 27, further comprising:
a nontransitory computing device configured to determine a concentration of carbon dioxide in the sample gas based on an electrical potential signal output from the first electrode and the second electrode.

* * * * *